United States Patent [19]

Donnell et al.

[11] Patent Number: 5,299,581
[45] Date of Patent: Apr. 5, 1994

[54] INTRAVAGINAL DEVICE

[76] Inventors: John T. Donnell, 7100 Pershing, St. Louis, Mo. 63130; J. W. Brown, 6 Briarcliffe Dr., Collinsville, Ill. 62234

[21] Appl. No.: 908,443

[22] Filed: Jun. 30, 1992

Related U.S. Application Data

[63] Continuation of Ser. No. 548,575, Jul. 5, 1990, abandoned.

[51] Int. Cl.$^5$ ....................... A61F 6/06; A61M 25/00
[52] U.S. Cl. ........................ 128/830; 128/834; 604/286
[58] Field of Search ............... 128/830–846; 604/285, 286, 278, 279

[56] References Cited

U.S. PATENT DOCUMENTS

| | | |
|---|---|---|
| 880,469 | 2/1908 | Rolfson-Schmidt . |
| 1,355,846 | 10/1920 | Rannells . |
| 1,401,358 | 12/1921 | Peterkin . |
| 1,575,123 | 3/1926 | Martocci-Pisculli . |
| 2,110,962 | 3/1938 | Munro ............................ 128/832 X |
| 2,938,519 | 5/1960 | Marco . |
| 3,091,241 | 5/1963 | Kellett .................................. 604/286 |
| 3,618,605 | 11/1971 | Glassman . |
| 3,731,687 | 5/1973 | Glassman . |
| 3,760,805 | 9/1973 | Higuchi ........................... 128/832 X |
| 3,760,806 | 9/1973 | Leeper ............................. 128/832 X |
| 3,762,413 | 10/1973 | Hanke . |
| 3,791,385 | 2/1974 | Davis . |
| 3,902,493 | 9/1975 | Baier et al. . |
| 3,995,634 | 12/1976 | Drobish ............................... 128/832 |
| 4,018,225 | 4/1977 | Elmi . |
| 4,034,756 | 7/1977 | Higuchi et al. .................. 128/832 X |
| 4,077,409 | 3/1978 | Murray et al. . |
| 4,286,596 | 9/1981 | Rubenstein . |
| 4,340,055 | 7/1982 | Sneider . |
| 4,553,965 | 11/1985 | Conn et al. . |
| 4,693,705 | 9/1987 | Gero .................................. 604/286 X |
| 5,002,540 | 3/1991 | Brodman et al. ............... 128/834 X |

Primary Examiner—Michael A. Brown
Attorney, Agent, or Firm—Rogers, Howell & Haferkamp

[57] ABSTRACT

A novel intravaginal device usable as a mechanism for introducing medicaments into the vagina of a human female. The device can be used for maintaining in the vagina medicaments and the like that otherwise might leak out and increasing the area of contact between the medicaments and the vaginal mucosa. At the same time it provides a device for the absorption of excess fluids.

27 Claims, 2 Drawing Sheets

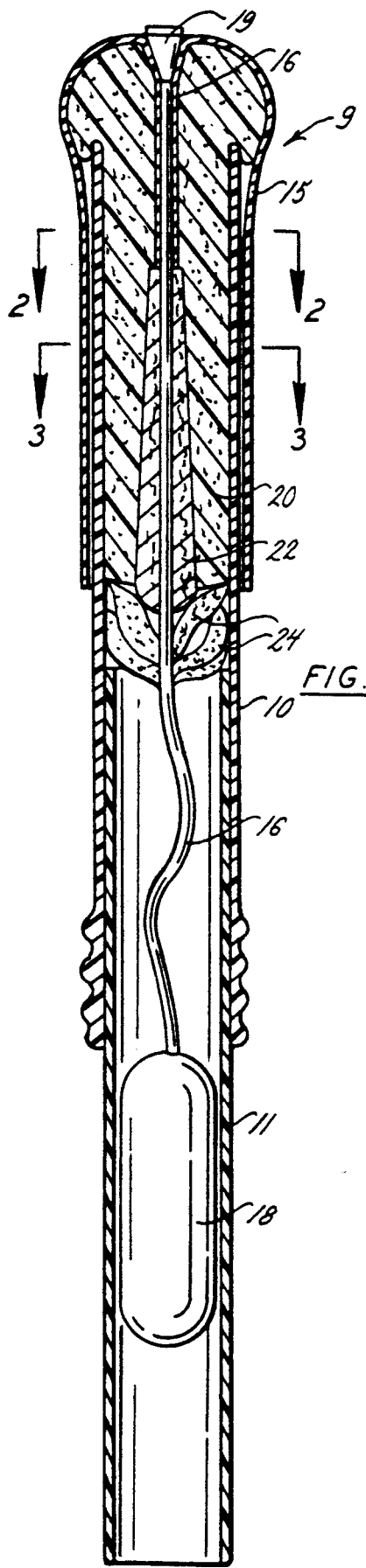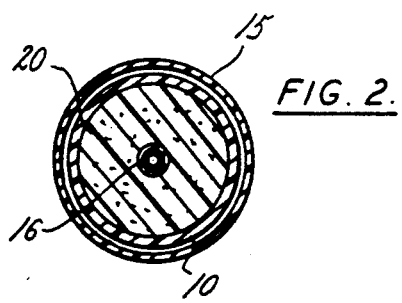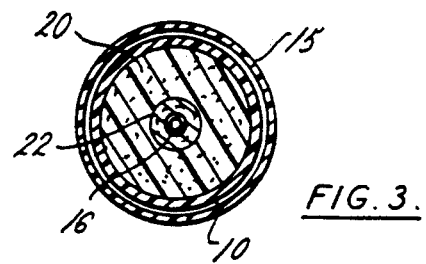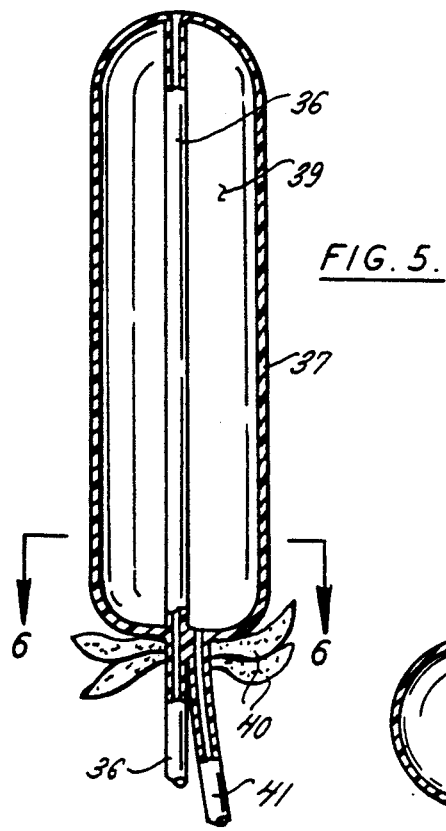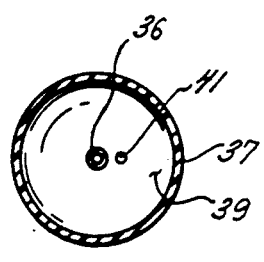

INTRAVAGINAL DEVICE

This is a continuation of copending application Ser. No. 07/548,575 filed on Jul. 5, 1990, now abandoned.

BACKGROUND OF THE INVENTION

1. Field of the Invention

The present invention relates to an intravaginal device (IVD) and more particularly to such device as means for introducing medicaments into the vagina of a human female.

2. Description of the Prior Art

To facilitate normal function or to assist in the recovery and restoration of tissues and organs that have deteriorated from traumatic or systemic changes, injury or infection, it is sometimes desirable to enhance the tone, health or function of the vagina, cervix and related organs and tissues through biological, chemical and/or physical action. In this connection, it is sometimes desirable to apply lubricants, medicines, topical anesthetics or other desensitizers, antiseptics, conditioners or other medicaments to the vagina.

Accordingly, various techniques have been developed to achieve such ends. For example, skin patches, injections and oral administration have been employed to medicate the targeted tissues. Such methods suffer from a variety of drawbacks including the involvement of entire body systems, the necessity for the frequent engagement of medically trained personnel, inconvenience and the absence of direct physical action on the affected tissues. Many women have found other conventional methods involving topical applications by means of reusable syringes inconvenient and uncomfortable. Such methods also typically require the user to lie down for application and tend to be unsanitary and messy in that the reusable syringe must be cleaned and the medicament and/or its carrier tends to leak from the vagina.

Prior art methods suffer from other disadvantages as well. In particular, it is noted that the walls of the vagina in its normal relaxed state comprise a number of folds of skin. Thus, medicaments applied according to conventional techniques tend to miss areas of the walls. Further, such techniques do not generally provide the maximum benefits that can be obtained by physical action directly on the tissues.

The prior art devices can be considered in three connections. The first of them is the type of device that is essentially contraceptive as represented by U.S. Pat. No. 4,553,965. Such devices consist of a tampon that can be inserted into the vagina and near the cervix and also a separate removable receptacle for liquids of a contraceptive nature that is injected into the tampon prior to its insertion into the vagina. Contraceptive devices obviously differ in several respects from the present case, and they must not be of such a nature to interfere with normal sexual intercourse.

A second type of device is the menstrual tampon that is primarily designed for preventing menstrual flow from escaping from the vagina during menses. These devices typically are not designed to supply medicaments to the vagina. These devices may be squeezed to a small size and expand when inserted thereby to seal off the Sometimes such devices have some form of medicament present but they are basically inapplicable to the invention of the present application. For example, U.S. Pat. No. 3,618,605 is a device made of elongated material that is folded up. The device contains no shield and no means of introducing medicaments at the time it is inserted. See also U.S. Pat. No. 3,731,687. U.S. Pat. No. 3,762,413 is basically the same type of device as the previously mentioned ones, save only that it provides means for mechanically expanding it. U.S. Pat. No. 3,791,385 includes a tube for admitting air to the interior of the device when it is desired to remove it.

The third class consists of devices that are actually designed to supply medicaments to the vagina. Such devices are represented by the U.S. Pat. No. 1,401,358 to Peterkin. This device is not supplied with a shield of the type employed in the present invention, and must be inserted by forceps.

The device of Rolfson-Schmidt U.S. Pat. No. 880,469 is similar to that of the foregoing patent but relies upon threadlike material to distribute the medicine. U.S. Pat. No. 1,575,123, to Martocci-Pisculli, requires an outer shell of a soluble material that dissolves after insertion, thereby exposing expansible material. No outer shell remains about this material. Medication may be applied at the top of the shell for application to the cervix, and medication may be applied to the absorbent expansible material within the shell. However, it is not seen how this device could retain a liquid medicament layer against the vaginal walls. Moreover, in that the expansible material is moisture absorbent, it appears that the material would work to absorb or withdraw the medicament from the vaginal walls.

Rannells U.S. Pat. No. 1,355,846 describes a device having a tube running into it through which medicines may be introduced. For obvious reasons, this device requires the service of a physician.

U.S. Pat. No. 4,077,409 to Murray is essentially a catamenial-type device for controlling menstrual flow. It is cited in this group only because it notes that disinfectants and medicaments can be added to the material filling the capsule. The device is obviously different from the present invention as will appear.

SUMMARY OF THE INVENTION

Briefly, therefore, the present invention is directed to a novel IVD usable as means for introducing medicaments into the vagina of a human female and holding such medicaments in contact with the vaginal mucosa. Basically the device can be used for maintaining in the vagina medicaments and the like that otherwise might leak out. At the same time it provides a tampon as a means for the absorption of excess liquids.

The device uses a familiar telescopic insertion mechanism for its being inserted into the vagina. It also includes a shield of relatively thin, flexible, membrane-like material such as a plastic that surrounds a pressure element, receives medicaments, holds the medicaments against the vagina walls and prevents their inadvertent contact with the pressure element or tampon material prematurely. To this end there is a tube that discharges outside of the shield at the top of the IVD or pressure element. This tube may be connected to an injection capsule or syringe that contains the medicament and it normally has a plug at the end that prevents it from discharging its material until desired. The pressure element is a material that can expand and cause the pressure element to fill and expand the vagina and to apply gentle pressure to the walls thereof. Further, there is an absorbent leaf tampon at the lower end of the pressure element. This is expansible against the walls of the vagina and acts as a means to prevent the escape of the medicaments or other liquids that are present. The device does not require the woman to lie down to apply medicaments and it does not involve the necessity of keeping clean and pure syringes and the like.

The foregoing arrangement enables the product to adapt itself to the shape of the vagina of a woman. The vagina is varying in shapes from the entrance to the cervix and it also varies in size. The present invention adapts to these variations. Moreover, the device expands the vagina, unfolding the walls thereof, permitting access for the medicament to sections of the walls that are otherwise concealed. In addition, the gentle pressure applied to the vaginal walls by the device provides beneficial physical action on the tissues, thereby to improve tonality and other aspects of the tissues and organs in question.

BRIEF DESCRIPTION OF THE DRAWINGS

FIG. 1 is an axial section through the device in its original state;

FIG. 2 is a sectional view taken along line 2—2 of the device of FIG. 1;

FIG. 3 is a sectional view taken along line 3—3 of the device of FIG. 1;

FIG. 5 is an axial section similar to FIG. 1 but of a second embodiment of the device;

FIG. 6 is a sectional view taken along line 6—6 of FIG. 5;

DETAILED DESCRIPTION OF THE PREFERRED EMBODIMENT

Figure 4:
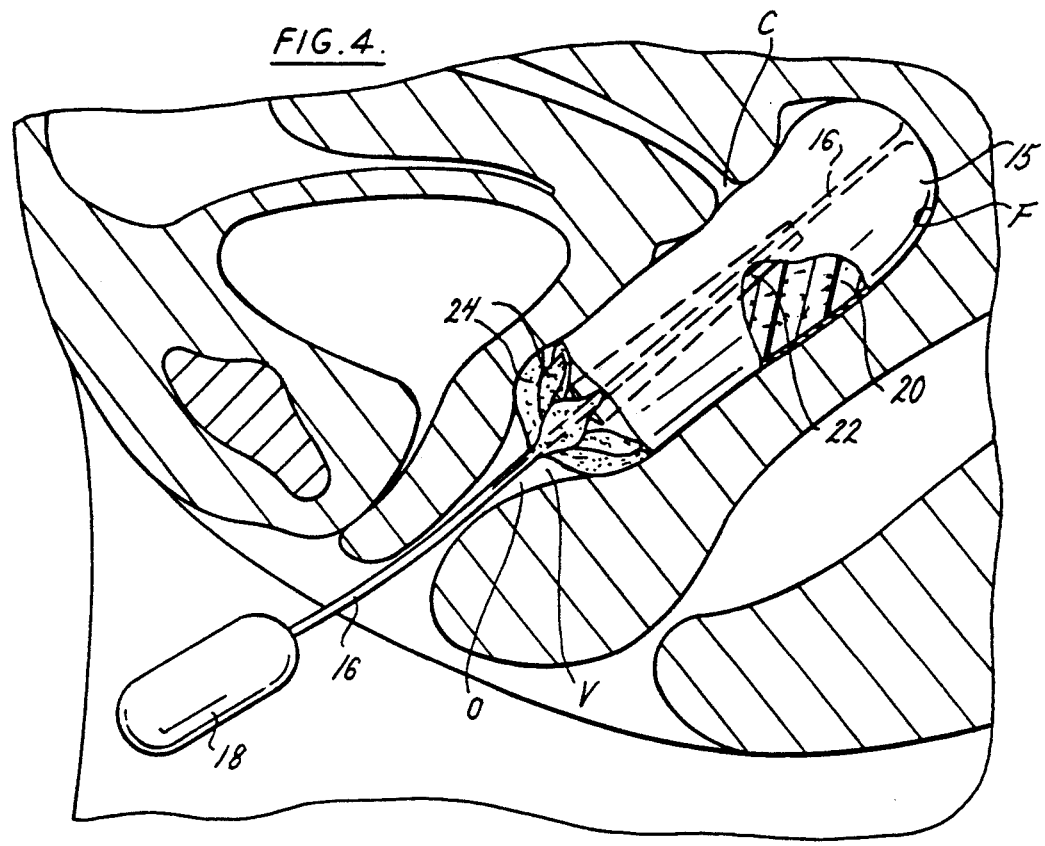
FIG. 4 is a section of the female pelvic region with the device in place.

Referring now to the drawings, and particularly, FIG. 1, shown generally at 9 is an intravaginal device (IVD) of this invention. The device is shown as being initially mounted in a telescopic-type of applicator tubing of the type that is generally used with tampons and which facilitates axial insertion of the device into the vagina. The applicator tubing consists of outer tube 10 and an inner tube 11. The IVD is mounted within the upper part of the outer tube 10.

The IVD 9 incorporates an outer shield 15 of a flexible, membrane-like material that may be the general shape of a fingerstall of approximately one and one-quarter inch diameter by three inches length from its apex A to its skirt S. Although the shield is shown in FIG. 1 as draping about the exterior of the upper end of outer tube 10, it will be understood that the IVD may be arranged such that the shield is situated within the upper end of the tube 10. The contact surface of the shield may be scarified or pocketed to facilitate contact between medicaments thereon, such as topically active ingredients, and the vaginal mucosa or walls. At its upper or proximal end (i.e., the end at the first inserted end of the device as it is inserted into the vagina), the shield 15 is connected to a tube 16 running axially therethrough. The other end of the tube 16 may be in turn connected to a capsule 18 for containing medicaments to be introduced into the vagina, such as lubricants or estrogen-containing materials used in the treatment of post-menopausal syndrome. The upper or proximal end of the tube 16 (i.e., the end connected to the shield 15) may be closed by a removable plug 19 to prevent the escape of the contents of the capsule 18 prior to use of the device. The plug may be of stopper-shape as shown in FIG. 1 or may be another type of seal, such as tape.

Within the shield 15 and within the upper or proximal end of the outer tube 10 is located a pressure element 20 that is of a cylindrical finger-shape of shape-restorative, compressible, non-reactive, human body-cavity-compatible, lightweight polyurethane foam or sponge, or any of a number of similar materials. It is about two to about four inches in length and about one-half to about two and one-half inches in diameter when measured in a relaxed state. The center of this pressure element 20 may be provided with a passage to accommodate a cord for easy withdrawal of the device from the body, as with standard tampons. The pressure element might also receive a frangible capsule therein instead of employment of capsule 18.

The entire pressure element 20 is enveloped in the shield 15 with the skirt of the shield extending below the lower end of the pressure element. Thus, even if the pressure element is a moisture absorbent material, the vaginal walls need not fight against this absorbency to maintain themselves within the medicament bath. The shield provides a moisture barrier between the absorbent material and the vaginal walls. Upon axial insertion into a vagina and release from the insertion tube 10 into which the IVD has been compressed, the pressure element attempts to regain its relaxed shape, thus filling the shield and expanding the vagina by exerting a gentle pressure upon the walls of the vagina so as to unfold and extend the vaginal walls for optimum contact with the shield and the intervening introduced substances. Additionally the gentle pressure exerted by the pressure element upon the vaginal walls may stimulate adjacent and underlying muscle tissue reaction, which may improve the tonicity of the vagina and adjacent organs.

As shown in the drawings, the pressure element 20 may have a conical recess extending upwardly from its bottom end. This recess receives a core such as a cone tampon 22 of lightweight cotton or other suitable, possibly absorbent material similar to that used for catamenial tampons. This is approximately two and one-fourth inches long and one-half inches in diameter at its bottom part. The core can be employed as an absorbent or as a stiffening means for adding rigidity to the device, or both. Immediately below the core there is an absorbent material, such as a sponge or leaf tampon 24 that is adapted to expand as shown in FIG. 1 when the confining effect of the tube 10 is removed. This insertion is done by moving the tube 10 inwardly into the vagina and then withdrawing a tube 10 while maintaining the tube 11 against the device. This leaf tampon engages the walls of the vagina to trap by absorption or barrier action flow of the liquids such as medicaments, vehicles therefor or vaginal exudates which otherwise might flow from the shield 15 and leak from the vagina. The cone tampon may further serve to absorb and prevent leakage of liquids whether excess medicament, medicinal vehicles, lubricants, body fluids, or other liquids, from the vagina during the period of IVD use.

The IVD of the present invention is shown in place in FIG. 4. It will be seen that it extends inwardly of the os O or open end of the vagina V and against the fornix F of the vagina V. The cervix C may extend at other angles to the vagina but as will be evident it can be accommodated in any of those by the present invention.

The invention as shown in FIG. 1 is ready to be inserted into the vagina of a user. To this end, the injection capsule is filled with medicaments adapted to be applied to the walls of the vagina. The plug 19 can then be withdrawn and the device inserted axially into the vagina by the conventional techniques for insertion of tampons. The applicator tubing can then be removed in accordance with such conventional techniques. Initially the pressure element 20 will expand owing to the relief of the confining pressure of the tube 10. This will cause it to apply modest pressure to the walls of the vagina. This expansion of the pressure element tends to expand radially outwardly the walls of the vagina which may even be quite close together before insertion of the present invention. The removal of the tubes 10 and 11 then leaves the injection capsule 18 accessible. The injection capsule 18 can be squeezed to cause liquid or other jelly-like material or the like to pass through the tube 16 to the outside of the shield 15. The injection capsule is normally sized to discharge the proper amount of liquid to coat the shield 15 to form a liquid layer between the shield and the walls of the vagina.

The arrangement minimizes leakage of the medicaments or other liquids from the vagina. However, it is not required that there will be a total elimination of such leakage in all cases. The presence of the absorbent leaf tampon and, optionally, absorbent cone tampon means that such leakage will normally be absorbed before it passes from the vagina.

FIG. 5 illustrates a second embodiment of the device, which employs different kind of expansion arrangement. In this case, the pressure element consists of an expansible member of generally cylindrical shape such as about one and a quarter inch in diameter by three inches in length. It is formed of very flexible but reasonably strong plastic material. The expansible member has a tube 36 extending through it and opening at the top end in the same manner as does the tube 16 of the earlier type. Alternatively, the tube 36 may extend along the side of the expansible member. In any event, the expansible member is surrounded by a shield 37 that is in effect the same as the shield 15 of the previous type. However, as opposed to the open skirt of the shield 15, the shield 37 connects to tube 36 at the lower end as well as at its upper end, thereby to form an axially extended, balloon-like structure, referred to hereinafter as an expandible member or bulb 39. As with the first embodiment, there is an absorbant such as the leaf tampon 40 that is similar to the one for the leaf tampon 24 of the previous description.

Figure 7:
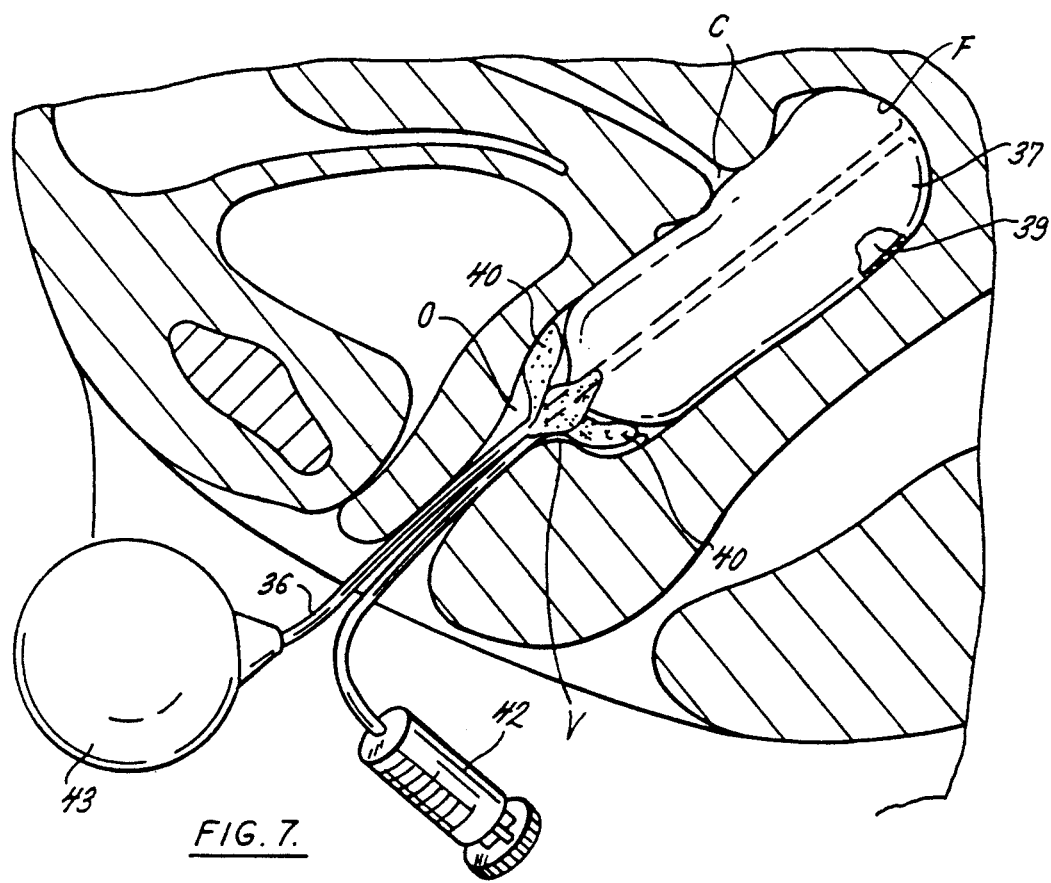
FIG. 7 is a view similar to FIG. 4 but of the second embodiment of the device.

In addition there is a tube 41 connecting from a supply 42 of fluid such as water or other liquid or gas that opens into the expandible member or bulb 39. If the tube 36 extends axially through the center of the bulb 39 as shown in FIGS. 5, 6 and 7, the bulb 39 is in the form of an axially extended, balloon-like torus structure, with the tube 36 extending through the central axis thereof and the tube 41 extending to the interior thereof. On the other hand, if the tube 36 extends along the side of the bulb 39, the bulb 39 is generally cylindrical in its expanded condition. Alternatively, tube 36 may be eliminated and the medicament may be applied in another manner. For example, the device may be compacted in its pre-expanded or deflated form and placed within a small receiving vessel shaped as a cup at the end of a rod. The medicament may then be placed as a glob on the compacted device. The device may be inserted into the vagina by means of the rod, the rod withdrawn and the device inflated. The action of insertion and inflation would then tend to spread the medicament over the shield of the device and tube 36 may thereby be unnecessary. In another form, the medicament may be applied by a syringe.

By any of these arrangements a charging member 42 (as shown in FIG. 7, which illustrates the second embodiment of the device in place in a vagina) can be activated to discharge liquid or gas into the expansible member 39 to cause it to fill the vagina and to seal off the cervix. As in the first embodiment, a capsule 43 may be provided for injection of medicament if a tube 36 (or other such mechanism) is employed for introduction of medicament. The shield 37 may be the outer surface of the bulb 39. Alternatively, a separate membrane-like material may be applied to the outer surface of the bulb 39 to form the shield 37.

In certain respects, this fluid activated embodiment may be preferable to the sponge-type embodiment. For example, this second embodiment might more readily adapt to asymmetries or inconsistencies in the vagina or the walls thereof. Thus, if the muscles associated with one portion of the walls are relatively strong while the muscles associated with another portion are relatively weak, the stronger portion may apply a force against the device and fluid therein to distort the device to apply greater pressure against the weaker portion, thereby to exercize the weaker muscles in compensation.

In the preferred construction, the filler material for the bulb 39 is gaseous. It is also preferably non-reactive gas that will not react with the body or with the medicaments. Such a gas would be air or carbon dioxide, for example. The incompressibility of liquid produces two disadvantages. The first is that the incompressibility limits the ability of the device to yield once it is set in place. Thus, it may be uncomfortable to the wearer. The other is that introduction of even a slight excess of a liquid risks rupture of the bulb 39, whereas a gas is compressible and so may allow great room for error in this respect. Also, a gas filled bulb might more sensitively adapt itself to the variations in shape and size of the vagina as indicated in the drawing.

In either of these two forms of the device, it will be understood that it may be inserted by being mounted into the telescopic tubes 10, 11, which are then removed. The insertion of the second embodiment may require an initial admission of a certain amount of fluid into the bulb 39 so that it may be inserted into the vagina. Alternatively or additionally, tube 36 may be of rigid material to aid insertion. Withdrawal of each device may be by standard techniques as employed in conjunction with standard tampons, such as by pulling a cord or the tube 36 attached thereto. I the fluid activated embodiment, it may be preferable to remove the fluid from within the device before withdrawal of the device from the vagina.

As the injection capsule in both cases is activated, the vagina is essentially cut off from leakage and the medicaments from the injection capsules are then effective to act on the vagina.

In view of the above, it will be seen that the several advantages of the invention are achieved and other advantageous results attained.

As various changes could be made in the above methods and devices without departing from the scope of the invention, it is intended that all matter contained in the above description and shown in the accompanying drawings shall be interpreted as illustrative and not in a limiting sense.

What is claimed is:

1. In an intravaginal device, a flexible member insertable into a vagina and formed of a thin, sheet-like material impervious to passage of vaginal fluid therethrough whereby to adapt itself to the shape of the vagina walls, means to cause the member to engage the walls of the vagina, means to conduct a medicament to the outside thereof after the member has been inserted into the vagina and is engaged with the vagina walls thereby to apply the medicament to the vagina walls, and means to restrict the escape of the excess fluids from the vagina.

2. The device of claim 2 wherein the member is shaped like a finger-cot with an opening in its proximal end through which medicament may pass, and removable means to close the said opening to prevent escape of the medicament prior to insertion into the vagina.

3. The device of claim 2 wherein the member is shaped like a finger-cot with an opening in its proximal end through which medicament may pass, the opening in the member is connected to a tube that extends outwardly of the member, the tube being adapted to receive medicament and to deliver the same to the outside of the member, and the member contains and expansible means in the form of a closed flexible bag of fluid, the tube extending through the closed body of fluid and there being a second tube extending to the interior of the expansible means whereby one may add to the fluid therein.

4. An intravaginal device comprising two telescopic tubes, one being smaller, the other being larger and being of a size to be inserted into a vagina, a pressure element within the larger of the two telescopic tubes, the pressure element being compressed and compacted and being expansible material when released form the larger of the two telescopic tubes; a shield of flexible material of a hood-like nature that extends outside of the pressure element and outside of the larger of the tow telescopic tubes; the shield having an elongated, cylindrical center portion that extends into and is held by the pressure element, the shield extending to approximately a short distance below the pressure element portion and terminating in an open end, the shield being a flexible material so that it can engage the walls of the vagina, the elongated, cylindrical center portion extending through the pressure element and past the open end of the shield and terminating in a connection to an injection capsule whereby to deliver medicament into the vagina from outside of the shield; the injection capsule being within the smaller of the two telescopic tubes and being in fluid communication with the elongated, cylindrical center portion to deliver medicament thereto, there being an absorbent core within the inner portion of the pressure element and an absorbent leaf tampon at the bottom of the pressure element, the elongated, cylindrical center portion passing through the absorbent core and the absorbent leaf tampon, the absorbent leaf tampon being expansible when removed from the larger of the two telescopic tubes, the pressure element being likewise expansible to urge the shield outwardly against the walls of the vagina, and the absorbent core being adapted to confine liquid that could otherwise leak from outside of the shield to below the shield to below the pressure tampon.

5. An intravaginal device as set forth in claim 4, further comprising means for trapping leakage of the medicament from the vagina.

6. An axially insertable intravaginal device for application of medicament to the walls of the human vagina, the device comprising:

means for expanding the vagina radially with the device inserted axially therein;

a flexible, membrane-like material which engages the walls of the expanded vagina, the material being adapted to provide a barrier between the expansion means and the walls of the vagina; and means for introduction of medicament between the membrane-like material and the walls of the vagina, said membrane-like material being impervious to transmission of the medicament therethrough;

the device being adapted such that the membrane-like material holds the medicament against the walls of the vagina.

7. An intravaginal device as set forth in claim 6 wherein the device has a first inserted end which is positioned toward the fornix with the device inserted in the vagina and a second inserted end which is positioned near the os of the vagina with the device inserted in the vagina, and the means for application of medicament comprises:

an axial passageway extending from the second inserted end of the device to the first inserted end; and means for injection of the medicament through the passageway from the second inserted end to the first inserted end of the device and outwardly from the passageway onto the membrane-like material.

8. An intravaginal device as set forth in claim 7 wherein the means for expanding the vagina comprises an expansible, pressure tampon-like material.

9. An intravaginal device as set forth in claim 7 wherein the means for expanding the vagina comprises means for injection of a fluid into an axially extended balloonlike structure thereby to inflate the balloon-like structure and the membrane-like material forms an outer layer of the balloon-like structure.

10. An intravaginal device as set forth in claim 7 wherein said membrane-like material adapts to the general contours of the walls of the vagina when the vagina is in the expanded condition.

11. A method for therapeutic treatment of the human vagina, the method comprising:

axially inserting an intravaginal device into the vagina;

expanding the vagina radially;

engaging and applying pressure to the walls of the vagina with a flexible, membrane-like material;

applying medicament between the material and the walls of the vagina after the material has engaged with and while pressure is applied to the walls of the vagina; and holding the medicament against the walls of the vagina maintaining for a desired period of time the pressure applied to the walls of the vagina with the membrane-like material.

12. A method as set forth in claim 11 wherein said device comprises means for collecting leakage of liquids from the vagina.

13. A method as set forth in claim 11 wherein the device has a first inserted end which is positioned toward the cervix when the device is situated in the vagina and a second inserted end which is positioned away from the cervix when the device is situated in the vagina, and the medicament is applied to the walls of the vagina by injecting the medicament through an axial passageway extending from the second inserted end of the device to the first inserted end and onto the membrane-like material.

14. An axially insertable intravaginal device for application of medicament to the walls of the human vagina, the device comprising:
- means for expanding the vagina radially to a selected degree of expansion and subsequently decreasing the degree of expansion with the device inserted axially therein;
- a flexible, membrane-like material which engages the walls of the expanded vagina, the material being adapted to provide a barrier between the expansion means and the walls of the vagina; and
- means for introduction of medicament between the membrane-like material and the walls of the vagina the device being adapted such that the membrane-like material holds the medicament against the walls of the vagina.

15. An intravaginal device as set forth in claim 14, wherein the means for expanding the vagina and subsequently decreasing the degree of expansion comprises an axially extended balloon-like structure and means for injection and withdrawal of a fluid into the balloon-like structure thereby to inflate or deflate, as desired, the balloon-like structure.

16. In an intravaginal device, a flexible member, insertable into a vagina and shaped like a finger-cot with an opening in its proximal end through which medicament may pass and with removable means to close the opening to prevent escape of the medicament prior to insertion of the member into the vagina, the member being formed of a thin, sheet-like material whereby to adapt itself to the shape of the vagina walls, means to cause the member to engage the walls of the vagina, means to conduct a medicament to the outside thereof after the member has been inserted into the vagina and is engaged wit the vagina walls thereby to apply the medicament to the vagina walls, and means to restrict the escape of excess fluids from the vagina.

17. In an intravaginal device, a member, insertable into a vagina and shaped like a finger-cot with an opening in its proximal end through which medicament may pass, the opening in the member being connected to a tube that extends outwardly of the member, the tube being adapted to receive medicament and deliver the same to the outside of the member and comprising means for withdrawal of the member from the vagina, means to conduct a medicament to the outside thereof after the member has been inserted into the vagina and is engaged with the vagina walls thereby to apply the medicament to the vagina walls, and means to restrict the escape of excess fluids from the vagina.

18. In an intravaginal device, a member, insertable into a vagina, the member being shaped like a finger-cot with an opening in its proximal end through which medicament may pass and containing an expansible means in the form of a closed flexible bag of fluid, the opening in the member being connected to a tube that extends through the closed body of fluid and outwardly of the member, the tube being adapted to receive medicament and deliver the same to the outside of the member, means to cause the member to engage the walls of the vagina, means to conduct a medicament to the outside thereof after the member has been inserted into the vagina and is engaged with the vagina walls thereby to apply the medicament to the vagina walls, means to restrict the escape of excess fluids form the vagina, and a second tube extending to the interior of the expansible means whereby one may add to the fluid therein.

19. The device of claim 18 wherein the member is the shape of a finger-cot or the like and wherein there is contained within it an expansible portion that can be expanded to cause the member to engage the walls of the vagina.

20. The device of claim 19 wherein the device contains a part that is initially constrained and which is releasable within the vagina to cause the part to expand and engage the member and cause it to fit against the walls of the vagina.

21. The device of claim 20 wherein the part comprises a compressible material that expands when it is released.

22. The device of claim 20 wherein the part contains also a portion that can receive liquid and which will absorb the same and thereby restrict its escape from the vagina.

23. A method forth in claim 22 wherein the portion comprises a section of material embodied within the portion and exposed near the distal end thereof whereby to receive and absorb liquid that otherwise could escape from the device into the vagina.

24. A method for therapeutic treatment of the human vagina, the method comprising:
- axially inserting an intravaginal device into the vagina, the device having a first inserted end which is positioned toward the cervix when the device is situated in the vagina and a second inserted end which his positioned away from the cervix when the device is situated in the vagina;
- expanding the vagina radially;
- engaging and applying pressure to the walls of the vagina with a flexible, membrane-like material;
- applying medicament between the material and the walls of the vagina after the material has engaged with and while pressure is applied to the walls of the vagina by injecting the medicament through an axial passageway extending from the second inserted end of the device to the first inserted end and onto the membrane-like material; and
- holding the medicament against the walls of the vagina and maintaining for a desired period of time the pressure applied to the walls of the vagina with the membrane-like material.

25. A method as set forth in claim 24 wherein the means for expanding the vagina comprises an expandable, pressure sponge-like material.

26. A method as set forth in claim 24 wherein the means for expanding the vagina comprises means for injection of a fluid into an axially extended balloon-like structure thereby to inflate the balloon-like structure and the membrane-like material forms an outer layer of the balloon-like structure.

27. A method as set forth in claim 24 wherein said membrane-like material adapts to the general contours of the walls of the vagina when the vagina is in the expanded condition.

* * * * *